United States Patent [19]

Muhammad et al.

[11] Patent Number: 5,650,174

[45] Date of Patent: Jul. 22, 1997

[54] COMPOSITION FOR PERORAL THERAPY OF COGNITION IMPAIRMENT AND A PROCESS THEREOF

[75] Inventors: Nouman Muhammad, Long Valley; Gary D'Alonzo, Somerville; Shirley Yang, Succasunna; Jay Weiss, East Brunswick, all of N.J.

[73] Assignee: Warner-Lambert Company, Morris Plains, N.J.

[21] Appl. No.: 400,774

[22] Filed: Mar. 7, 1995

Related U.S. Application Data

[63] Continuation of Ser. No. 957,322, Oct. 6, 1992, abandoned.

[51] Int. Cl.⁶ ................................................. A61K 31/44
[52] U.S. Cl. ................................... 424/494; 514/357
[58] Field of Search ............................ 514/357; 424/494

[56] References Cited

U.S. PATENT DOCUMENTS

| | | | |
|---|---|---|---|
| 4,113,882 | 9/1978 | Okazaki et al. | |
| 4,786,648 | 11/1988 | Bergmeier et al. | 514/357 |
| 4,853,230 | 8/1989 | Lovgren et al. | 424/466 |
| 4,882,169 | 11/1989 | Ventouras | 424/493 |
| 4,925,674 | 5/1990 | Giannini et al. | 424/469 |
| 4,925,675 | 5/1990 | Giannini et al. | 424/469 |
| 5,045,321 | 9/1991 | Makino et al. | 424/475 |
| 5,084,287 | 1/1992 | Ghebre-Sellassie et al. | 424/495 |
| 5,213,811 | 5/1993 | Frisbee et al. | 424/493 |
| 5,362,860 | 11/1994 | Huang et al. | 536/4.1 |
| 5,424,301 | 6/1995 | Huang et al. | 514/60 |

FOREIGN PATENT DOCUMENTS

| | | | |
|---|---|---|---|
| 0377518 | 7/1990 | European Pat. Off. | A61K 9/52 |
| 9407493 | 10/1992 | WIPO . | |

*Primary Examiner*—Marianne M. Cintins
*Assistant Examiner*—Keith MacMillan
*Attorney, Agent, or Firm*—Michael J. Atkins

[57] ABSTRACT

A solid composition for peroral therapy of cognition impairment is formulated to stabilize the acid labile drug, CI-979 HCl, by layering a mixture of thereof with a binder on mini-sugar spheres, and finally covering the structure with a protective coating.

7 Claims, 1 Drawing Sheet

COMPOSITION FOR PERORAL THERAPY OF COGNITION IMPAIRMENT AND A PROCESS THEREOF

This is a continuation of application Ser. No. 07/957,322 filed on Oct. 6, 1992, now abandoned.

FIELD OF INVENTION

The present invention is generally related to solid oral formulations of the drug CI-979 HCl, a cognition activator useful for the treatment of age-associated memory impairment and primary degenerative dementia, and a process of manufacturing said formulations, wherein the active ingredient is captured on small sugar seeds in binder-containing layers covered over all by a protective film coating.

BACKGROUND OF INVENTION

The compound CI-979 is a newly discovered cognition activator as described in U.S. Pat. No. 4,786,648 which disclosure is herein included by reference in the present specification. The compound CI-979 has been discovered as having pharmacological properties that make them useful as cognition activators. Therefore, the compound has been under consideration for therapy of age-associated memory impairment and primary degenerative dementia. Furthermore, CI-979 HCl is being developed for the treatment of Alzheimer's disease.

Specifically, CI-979, has the following structural formula (A):

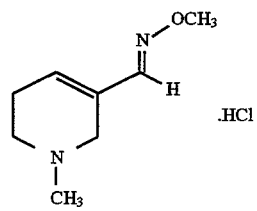

As can be seen in formula (A), CI-979 contains a methyloxime group attached to a basic tetrahydropyridine ring (1,2,5,6-tetrahydro-1-methyl-3-pyridine methyloxime). Similar to other pyridine derivatives, the free base form of CI-979 is a volatile liquid, whereas CI-979 hydrochloride is a stable white crystalline salt.

In the course of preformulation testing, the storage stability of the drug and aqueous solutions of CI-979 HCl has been studied by exposure to heat, UV light, and the pH range (see FIG. 1). Specifically, it has been found that the HCl salt will convert in the presence of basic or neutral solid excipients to a free base form in the air and consequently evaporate. Furthermore, in acidic environments of less than pH5 the drug undergoes hydrolysis to an aldehyde degradation product. Acid labile compounds such as CI-979 thus require a special formulation in order to serve effectively as a pharmaceutical oral dosage. The acid hydrolyzed products of the drug CI-979 HCl are virtually devoid of any biological activity.

For the purpose of overcoming acid lability of the drug, one skilled in the art is acquainted with a number of acid protective formulations.

U.S. Pat. No. 5,045,321 discloses a stabilized pharmaceutical preparation (col. 14, Ex 8) wherein nonpareils are dust-coated using an aqueous hydroxypropylcellulose spray as binder, followed by an enteric coating.

U.S. Pat. No. 4,882,169 describes coated pellets having a core comprising at least one active ingredient, optionally, one or more intermediate layers, and a swellable outer layer. The core is defined as containing optional excipients as, e.g., binders, plasticers, glidants, absorbing substances and/or swellable materials.

U.S. Pat. No. 4,853,230 discloses pharmaceutical oral formulations of acid-labile substances. In particular, a pharmaceutical dosage form is formulated to prevent substances from coming in contact with gastric juice. An alkaline core is thus coated with enteric coating, e.g., with cellulose acetate phthalate, permitting dissolution and absorption within the proximal portion of the small intestine.

European Patent Application No. 0377518 A2 for sustained release pharmaceutical composition of a spheroidal core element composed of at least one active ingredient, and core coatings soluble to varying degrees at different pH ranges directed to a therapeutic effect over an extended period of time.

However, these methods are deficient in providing stability to dry triturates of a drug such as CI-979 HCl which is both rapidly degraded under acidic conditions and lost by evaporation under neutral or alkaline conditions due to conversion to the volatile free base.

SUMMARY OF THE INVENTION

It has surprisingly been discovered that the volatilization effect of neutral excipients may be effectively diminished by minimizing contact of the alkaloid methyloxime drug with excipients by means of a plurality of layers of combinations of the drug and a binder onto nonpareil seeds. Specifically, the present invention provides a vehicle wherein the alkaloid methyloxime drug is mostly surrounded by binder moieties. It has also been discovered that the preservative layering feature is enhanced by using an appropriate ratio of binder to drug ranging of about 20/1 to 0.25/1. In addition, a protective external film layer is provided. A process according to the present invention is described.

The present invention is, in particular, directed to a stable solid oral dosage form of the cognition activator, CI-979 HCl wherein the starter seeds or nonpareils (tiny decorative sugar spheres) are used as solid vehicle or base for a mixture of CI-979 HCl as the active ingredient, hydroxypropyl cellulose as the binder, and talc as anti-adherent. Moreover, the present invention is specifically directed to pellets wherein the protective film coating comprises a water-soluble film-forming component, or anti-adherent, and a plasticizer.

The most preferred embodiment of the present invention comprises about 0.62% (w/w) of the drug CI-979 HCl about 96.8% (w/w) sugar granules, about 0.31% (w/w) hydroxypropyl cellulose as binder, about 1.5% (w/w) hydroxypropyl methylcellulose as film component, about 0.45% (w/w) talc as anti-adherent, and about 0.25% (w/w) polyethylene glycol as plasticizer.

Accordingly for the present invention, a method for preparing the oral pharmaceutical composition as described in detail below, comprises layering repeatedly the drug and binder mixture described above onto a solid carrier surface followed by at least one external or protective film coat.

DETAILED DESCRIPTION OF THE INVENTION

Figure 1:
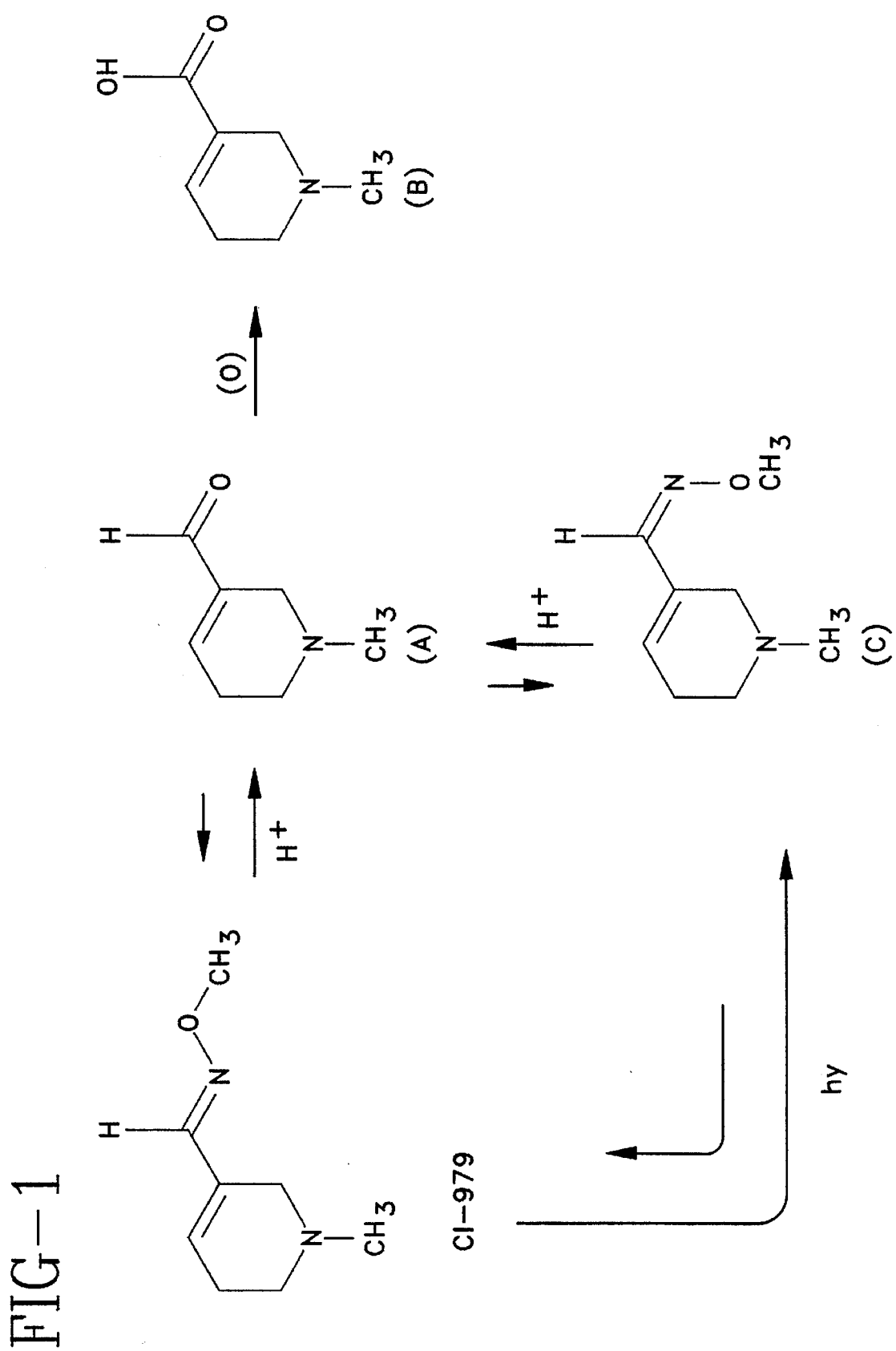
FIG. 1 is given to illustrate the putative degradation pathways and degradation products of CI-979 HCl

The chemical properties of the active compounds as heretofore discussed clearly indicate that protection from acidic environment is necessary for an effective pharmaceutical dosage. According to the present invention, alkaloid ether methyloximes such as the cognition activator, CI-979 HCl can be formulated into stable solid oral dosage forms.

As will be readily apparent to one skilled in the art from what is said about the chemical properties of CI-979 HCl illustrated in FIG. 1, an oral dose formulation of the alkaloid drug must be protective for storage and should prevent the conversion of CI-979 HCl to the inactive aldehyde by hydrolysis or to the volatile free base with subsequent mass erosion from the composition due to evaporation. Thus, for the purpose of safe, intact peroral delivery, the present invention provides for a stabilizing pharmaceutical system wherein the preferred active ingredient, CI-979 HCl is contained at a suitably low concentration combined in a mixture with a binder.

The binder is selected from polymers such as, e.g., hydroxypropyl cellulose at concentrations ranging by weight from about 1% to about 5% of the active aqueous mixture. This active ingredient/binder mixture or active layer mixture can further contain a suitable amount of dispersant such as talc. The active binder mixture is thus applied in layers on a plurality of solid, inert core surface. Moreover, the active mixture preferably comprises several layers in sufficient number such that each succeeding layer has progressively less contact with the core surface but is instead associated substantially only with the components of the active mixture.

The main function of the final outside coating is to provide adequate protection for the active layers from the subsequent processing. For that purpose, it is preferred to cast at least one film layer comprising substances suitable for providing a protective or seal coating and assuming safe delivery of the drug. Among such suitable substances are hydroxypropyl cellulose, hydroxypropylmethyl cellulose, polyvinylpyrrolidone and the like. Accordingly, the coating film or layer composition can include enteric coating polymers as provided by, e.g., cellulose acetate phthalate, hydroxypropyl methyl cellulose phthalate, polyvinyl acetate phthalate, and similar substances as known in the art to fashion enteric coatings. The extension coating can also include pharmaceutically acceptable plasticizers including those selected from among the polyethylene glycols at certain optimal concentrations. Finally, according to the present invention, it has also been found useful to add a dispersant component such as talc or colorants to the enteric film coat.

The solid core surface of the drug delivery system is provided by solids which are preferably inert, but water-soluble. The solid core matrix is more preferably in the form of microdiameter spheroidal solids. The core materials may be sugar, crystals or powder, sugar-based or other pharmaceutically acceptable polymers or aggregates. Moreover, the immediate, microscopic surface environment thereof should essentially be dry and have a pH of not less than about 5. Specifically, the pellet cores are indicated as being sugar spheres, balls, spheroidal solids or granules, i.e., nonpareils.

The purpose of the present formulation is to minimize the intimate contact of the acid and base labile drug with the other excipients. Therefore, a solution of the drug in a mixture with a binder is layered repeatedly on the sugar spheres such as nonpareil seeds. Consequently, only the initial layers are in intimate contact with the surfaces of sugar seeds. Increasingly, the subsequent layers consist substantially of drug and binder alone. In fact, the preferred embodiment includes several layers of the active ingredient binder mixture for an effective dosage.

A further aspect of the present invention provides a binder in relatively high proportion to the drug. The use of high proportionate levels of binder enhances the enclosure and entrapment of the active ingredient molecules. Consequently, the active ingredient is advantageously protected from any charges or other intermolecular forces which may be due to the molecular moieties extending from the core sugar surface, since as explained above, the alkaloid drug CI-979 HCl is unstable on prolonged contact with most acidic, neutral or basic excipients even in solid form.

The preferred overall ranges of the ingredients in the preferred peortal compositions are formulated by weight as follows: drug, about 1% to about 50%; sugar spheres (nonpareils), about 50% to about 99%; hydroxypropyl cellulose, about 0.25% to about 25%; hydroxypropyl methylcellulose, about 0.0% to about 5%; talc, about 0.0% to about 5%, and polyethylene glycol, about 0.0% to about 5%. Moreover, the most preferred formulation is composed of about 0.62% drug, about 96.87% sugar spheres, about 0.31% hydroxypropyl cellulose, about 1.5% hydroxypropyl methylcellulose, about 0.45% talc, and about 0.25% polyethylene glycol.

The invention is further illustrated in detail by, but not limited to, the following example for preparing a solid pharmaceutical composition comprising CI-979 HCl

EXAMPLE

In a preferred method for preparing the drug pellets, five (5) kg of nonpareil seeds (20–25 mesh size) are charged into the Glatt GPCG-5 rotor-granulator. Then the drug solution is layered onto sugar spheres (i.e., nonpareils) by using a tangential spray mode. Specifically, the layering solution is approximately composed of the drug (32.0 g); hydroxypropyl cellulose (16 g); talc (10.6 g), and water (600 ml).

Immediately following the drug layering process, the film-coating solution is sprayed onto the drug pellets. The composition of the film coating solution preferably comprises about 77.0 g hydroxypropyl methylcellulose; about 12.9 g polyethylene glycol; about 12.9 g talc; and about 1180 ml water.

After the completion of the coating step, the pellets are fluid-bed dried at a product temperature of 40°–45° C. for 20 minutes using the above-described equipment. Finally, the dry, coated pellets are finished by passage through a 16 mesh screen in order to remove any agglomerates. The parameters of the conditions applied for the different layering steps are itemized in Table I.

The stability of the instant formulation was successfully demonstrated in accelerated stress storage tests by higher temperature (60° C.) as listed in Table II.

TABLE I*'

| Parameters | Drug Layering | Film Coat |
|---|---|---|
| Bed Load (kg) | 5.0 | 5.0 |
| Spray rate (mL/min) | 8–10 | 15–20 |
| Atomizing air (bars) | 1–2 | 2.5 |
| Preheat (°C.) | 35–37 | 37 |
| Inlet (°C.) | 32–35 | 32–34 |
| Product bed (°C.) | 35–37 | 36–37 |
| Outlet (°C.) | 27–28 | 29–30 |
| Air velocity (m³/hr) | 160–175 | 130–150 |
| Rotor speed (rpm) | 250 | 250 |

TABLE II

| | | Percent Remaining | |
|---|---|---|---|
| Time (Weeks) | Temperature (°C.) | XP147051 | XP164061 |
| 1 | 60 | 100.0 | 98.95 |
| 2 | 60 | 98.92 | 100.00 |
| 4 | 60 | 100.0 | ND[1/] |

*/Processing parameters for CI-979 pellet formulation using the GPCG-5 with rotor insert.
[1/]ND = Not determined Any variations of the invention described above are not to be regarded as a departure from the spirit and scope of the invention as claimed.

What is claimed is:

1. A stable solid oral pharmaceutical composition for cognition activation comprising:
   (a) a core comprising a sufficiently inert granular substance;
   (b) an effective amount of a material comprising a cognition activating alkaloid ether methyloxime salt having the formula:

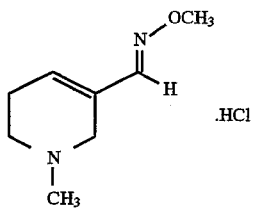

as active ingredient, in a layered mixture with a compound suitable for binding to the core substance, wherein the binder to drug ratio ranges from about 20/1 to about 0.25/1; and
   (c) a protective outer film layer.

2. The stable solid oral pharmaceutical composition as claimed in claim 1 wherein, in (b), the effective amount of material comprises a plurality of layers of the active ingredient/binder mixture.

3. A stable solid storage formulation of a cognition activating drug having the formula:

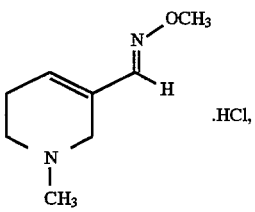

comprising a plurality of core entities covered by layers comprising the drug in a mixture with a suitable binder, wherein the binder to drug ratio ranges from about 20/1 to about 0.25/1, and further covered with a coating of film.

4. The stable storage formulation of claim 3 wherein the drug mixture further comprises an antiadherent compound.

5. A method for preparing a stable solid oral pharmaceutical composition for cognition activation therapy the method comprising the steps of preparing a solution comprising a binder and a drug having the formula:

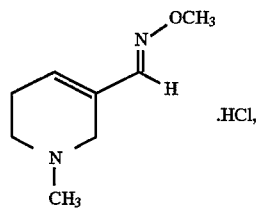

the solution having a binder to drug ratio ranging from about 20/1 to 0.25.1; and repeatedly layering binder/drug composition on 20–25 mesh nonpareil seeds, thereby sequentially diminishing direct contact between drug and nonpareil seeds.

6. A method for preparing the solid oral pharmaceutical composition of claim 1 comprising the steps of:
   (a) charging nonpareil seeds in a rotor-granulator;
   (b) layering a mixture of a drug having the formula:

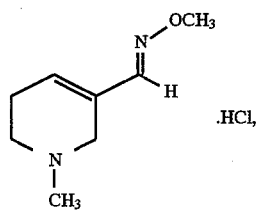

binder and antiadherent in water onto the nonpareils seeds using a tangential spray mode to form drug pellets; further,
   (c) spraying an aqueous protective film coat solution onto the drug pellets, said protective film coating comprising at least one of a water-soluble film forming component, a plasticizer and an adherent;
   (d) fluid-bed drying the coated drug pellets in the rotating granulator; and
   (e) passing the drug pellets through a particle screen.

7. The method of claim 6, wherein step (b) is repeated numerous times before applying step (c).

* * * * *